United States Patent [19]
Fritch

[11] Patent Number: 4,685,920
[45] Date of Patent: Aug. 11, 1987

[54] INTRAOCULAR LENS

[76] Inventor: Charles D. Fritch, Rte. 11, Box 239B, Bakersfield, Calif. 93308

[21] Appl. No.: 824,800

[22] Filed: Jan. 31, 1986

[51] Int. Cl.⁴ .............................................. A61F 2/16
[52] U.S. Cl. ...................................................... 623/6
[58] Field of Search ........................................... 623/6

[56] References Cited

U.S. PATENT DOCUMENTS 4,244,060  1/1981  Hoffer ..................................... 623/6
4,412,359  1/1983  Myers ..................................... 623/6
4,485,499 12/1984  Castleman ............................. 623/6

FOREIGN PATENT DOCUMENTS 0128784 12/1984  European Pat. Off. ................ 623/6

Primary Examiner—Ronald L. Frinks
Attorney, Agent, or Firm—Singer & Singer

[57] ABSTRACT

A lens implant for use by surgeons as a replacement for a person's cataractic lens. The lens implant having a curved side and a plano side and in which the plano side has at least two arcuate ridges of variable height that varies from a minimum height at each end to a maximum height at the centermost portion. Each of the arcuate ridges also has an arcuate shape measured from the anterior side to the posterior side.

5 Claims, 10 Drawing Figures

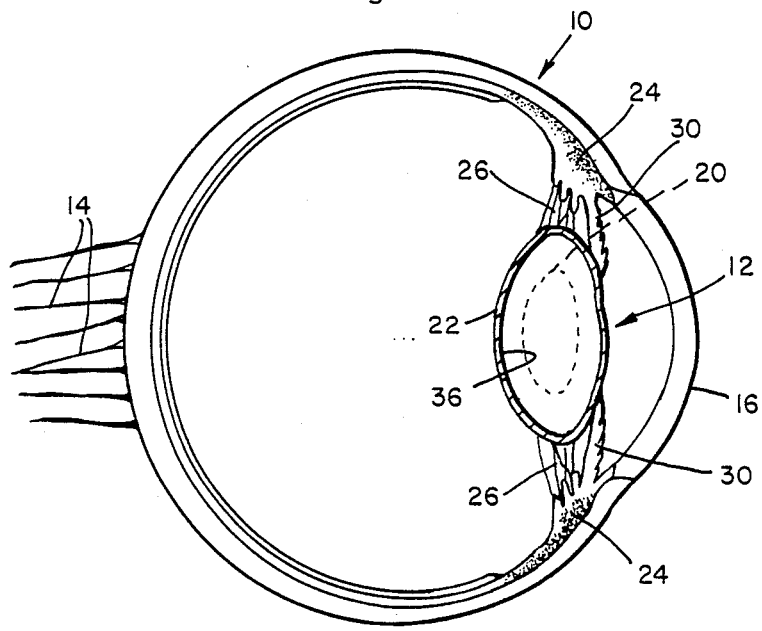
Fig. 1.
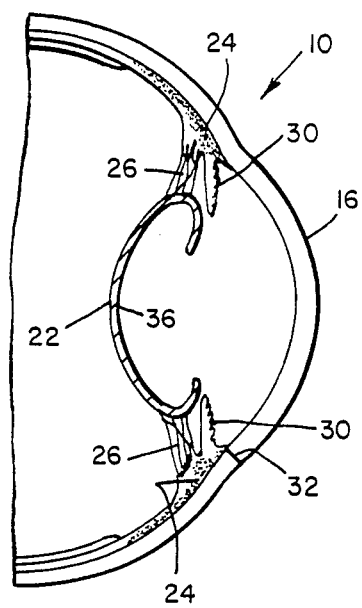
Fig. 2.
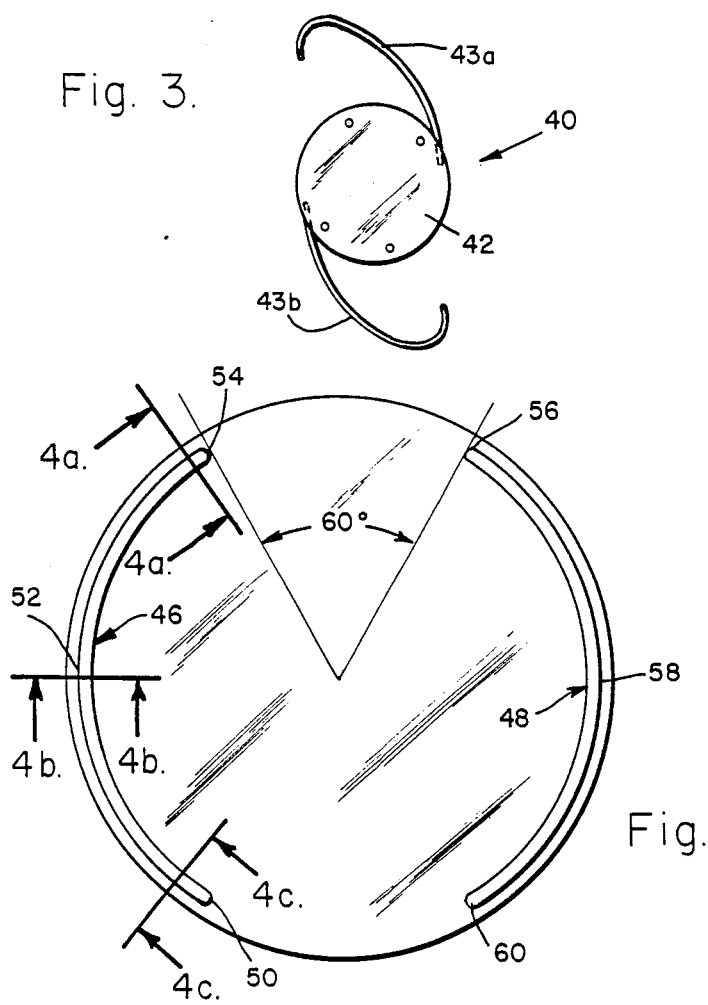
Fig. 3.
Fig. 4.

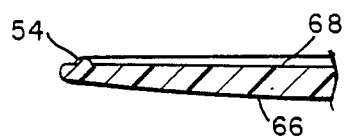
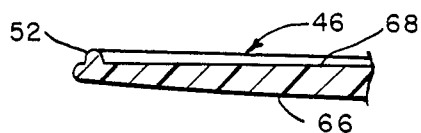
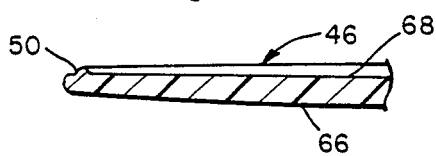
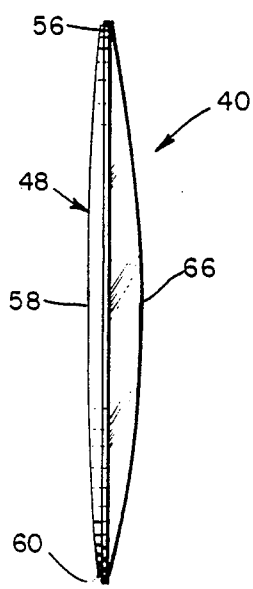
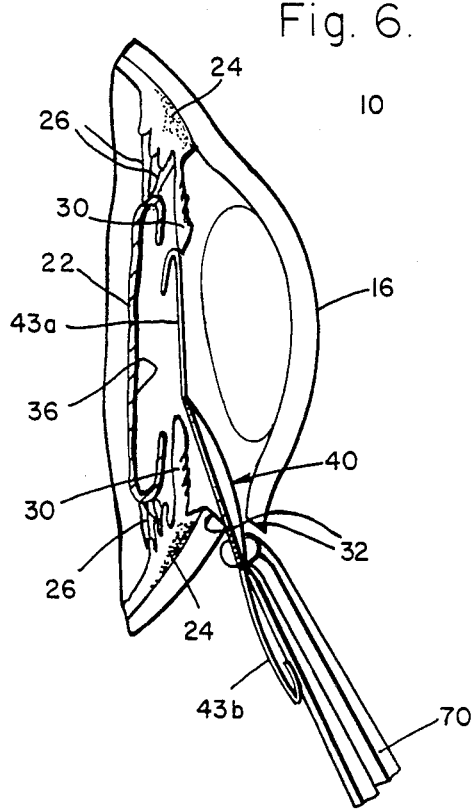
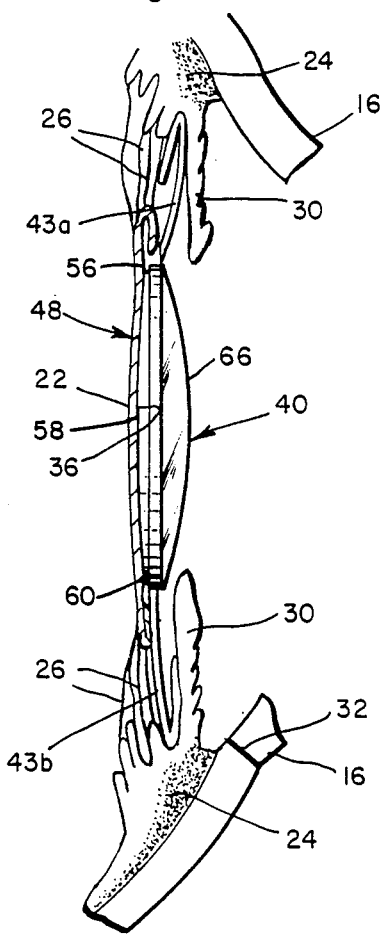

INTRAOCULAR LENS

This invention relates to an improved intraocular lens, also called an IOL lens, and more particularly a lens having a preferred shape that requires a smaller incision for insertion that is easier to handle by the surgeon and one that produces minimum irritation to the iris when inserted by the surgeon.

In the art as practiced today, the IOL lens has found great popularity among ophthalmologists and patients alike for the treatment of cataracts which have the effect of clouding over and becoming opaque, thereby preventing the patient from seeing.

In the normal eye the lens is encased within a capsule and held by a plurality of strands called zonules that are in turn attached to ciliary muscles attached to the wall of the eye. The zonules in effect comprise a plurality of strands that radiate from the periphery of the capsule and tend to hold the capsule in the center, thereby helping to center the capsule within the eye and at the same time to allow the capsule and the lens to move and focus in response to the varying light conditions.

A cataract condition is sometimes defined as a general loss of transparency in which the lens which is located within the capsule becomes opaque thereby preventing light from passing through to the optic nerve. The more opaque the lens the less vision for the patient.

The present-day treatment for cataracts involves the cutting of the anterior portion of the capsule coupled with the removal of the nucleus and the cortex of the lens located within the capsule. The surgeon leaves the posterior portion of the capsule in place and ensures that all portions of the cortex and the nucleus of the opaque lens have been removed.

In the art as practiced today, the IOL or lens implant is inserted within the capsule and maintained in position by means of springlike fingers called haptics that are attached to the IOL lens.

Present-day implants favor the use of posterior connections, which means that the lens is located behind the iris and in close proximity to the posterior portion of the capsule.

It has since been discovered that the plano surface of the IOL lens, when placed in direct contact with the posterior portion of the capsule, eventually adheres to the capsule's surface. Certain enzymes called T-non pearls tend to migrate between the plano surface of the IOL lens implant and the posterior surface of the capsule.

The T-non pearls have the dilatorius effect of becoming opaque and again interfering with the transmissivity of light through the patient's eye. The common treatment for removing the opacity effect of the T-non pearls is to use a laser commonly known as the Yag laser.

The Yag laser is an extremely powerful laser that is focused on the capsule and is designed to rip the hole in the capsule where it has gone opaque, thereby allowing light to again pass through and impact on the optic nerve. Unfortunately the effect of the Yag laser also destroyed the plano surface of the IOL lens implant, having the effect of destroying the plano surface and interfering with the focusing effect of the lens itself.

The art generally recognizes the efforts of Dr. Kenneth Hoffer of Santa Monica who designed an IOL lens implant with a ring in the form of a shoulder completely around the plano surface edge. The shoulder was originally designed to prevent the migration of the T-non pearls. The effectiveness of the shoulder to stop migration of the T-non pearls is not generally accepted by the authorities in the field, however, the ridge designed by Dr. Hoffer did have the effect of maintaining the plano surface of the IOL lens from contacting the posterior surface of the capsule. The space between the IOL lens and the posterior surface of the capsule has allowed the ophthalmologist to use the Yag laser to destroy the opacity caused by T-non pearls and without destroying the palano surface of the IOL lens.

Unfortunately, the shoulder or ring now located on the plano surface of the IOL has created additional problems for the surgeon when inserting the lens implant.

Specifically, the incision must be made larger to allow the ring to pass through, thereby increasing the chance of infection.

Grasping the implant during insertion has created problems for the surgeon due to the shoulder that causes the lens to move or tiddle during the operation. This phenomena has been called tiddly-wink by those skilled in the art and refers to any uncontrolled movement of the lens while being held in position by the surgeon during insertion of the implant in the eye. Obviously the tiddly-wink effect is very dangerous for the patient and for obvious reasons.

Lastly, insertion of the shoulder into the posterior chamber of the eye which is behind the iris means that the implant with the shoulder must pass over the iris on one side and then pass over the iris again when finally being inserted in place.

Considering that the iris is a very sensitive tissue, it can be appreciated that the shoulder on the implant has the effect of traumatizing the iris by irritating the iris as the shoulder passes over the iris when located in place by the surgeon and has caused the iris to bleed or even to rip during the operation. In many cases this traumatizing of the iris has caused the iris to contract during the operation even though the iris has been previously dilated with Miacol or other suitable materials, thereby making it harder for the surgeon to continue the operation.

In the present invention all of the objections and disadvantages of the prior shoulder have been eliminated and the new IOL lens implant can now be inserted by the ophthalmologist with less irritation to the iris, without the tiddly-wink effect caused by prior implants, and a minimum-size incision is needed, thereby substantially reducing the chance of infection.

The present objects and advantages are achieved by designing an IOL lens implant having a pair of annular rings located on the plano surface. The pair of rings are completely separated at both ends, thereby allowing room for the surgeon to hold the implant where there is no ring. Each annular ring is rounded from the anterior surface to the posterior surface and the height is variable from a minimum at each end to a maximum at the center and again decreasing to a minimum at the opposite end.

The variable height annular rings allow the surgeon to grasp the implant at a position in between the annular rings and to slide the implant through the incision as the variable height ridges cam the incision open in a smooth and continuous fashion. Sliding the implant over the iris is also done with a minimum of irritation and traumatizing as a result of the variable height rings camming the iris over the ring, both when the implant is located over the iris, and when finally located in position in the posterior chamber behind the iris.

The variable height annular rings also maintain the plano surface of the implant in a spaced-apart relationship with respect to the posterior wall of the chamber, thereby allowing the use of the Yag laser should that treatment be necessary in the future.

Further objects and advantages of the present invention will be made more apparent by referring now to the drawings wherein:

FIG. 1 is a cross-section of the eye showing the relationship of the lens, the cornea and the iris and supporting muscles;

FIG. 2 is a cross-section of the eye showing the position of the capsule after the surgeon has removed the nucleus and the cortex of the lens;

FIG. 3 is a plan view of the lens implant constructed according to the present invention;

FIG. 4 is a plan view of the lens implant showing the plano side;

FIGS. 4a, 4b and 4c are partial sectional views illustrating the variable height ridge on the plano side of the lens;

FIG. 5 is a side view of the lens illustrating the variable height ridge;

FIG. 6 is a cross-section of the eye illustrating how the surgeon inserts the lens implant in the posterior chamber behind the iris; and FIG. 7 is a cross-section of the eye showing the implant in its final position with the variable height ridge adjacent the capsule.

Referring now to FIG. 1, there is shown a cross-section of the eye 10 illustrating the lens 12, the optic nerve 14 in the posterior portion, and the cornea 16 located in the interior portion of the eye.

The lens 12 comprises a nucleus 18 and a cortex 20 all located within a capsule 22. The lens 12 actually comprises the nucleus 18, the cortex 20 and the capsule 22 which is suspended from the ciliary muscles 24 by a plurality of spidery filaments called zonules 26.

The zonules 26 maintain the lens 12 in a centermost portion thereby preventing drooping of the lens and at the same time holds the lens in a flexible suspension system that allows the lens to contract and expand and focus as determined by the needs of a visual image.

Normally the lens 12 is transparent and is free to change shape and focus light passing through the cornea 16 and focus the light onto the optic nerve 14. In time, however, the lens 12 becomes opaque and that includes the nucleus 18 and the cortex 20, thereby effectively blocking the passage of light to the optic nerve and preventing the patient from seeing. In this situation it is necessary for the surgeon to remove the nucleus 18 and the cortex 20, thereby removing that portion of the lens that has become opaque and prevents light from passing to the optic nerve 14.

The opaqueness of the nucleus 18 and the cortex 20 is generally referred to as a cataractic lens or, in other words, a cataract.

It is important to note that the cataract is not a film or covering over the lens but, rather, it is the lens itself in the form of the nucleus 18 and the cortex 20 that has become opaque that must be removed.

FIG. 1 also illustrates the position of the iris 30 that is generally cylindrical in shape and holds the lens 12 in the posterior chamber. The iris 30 is very tender and is that portion of the eye that we see as having a color, whether it be blue or brown and contains the pigment which we call color.

Referring now to FIG. 2, there is shown a cross-sectional view of the eye 10 which contains an incision 32 located on the side of the cornea 16 through which the surgeon has inserted his instruments into the anterior chamber 34 to effect removal of the cortex and the nucleus, leaving only the posterior section 36 of the capsule 22.

FIG. 2 shows the condition of the eye as it is prepared for the IOL lens implant to be placed within the capsule 22 and against the posterior portion 36.

Referring now to FIG. 3, there is shown an IOL lens implant 40 containing the optic portion 42 and a pair of haptics 43 that are used to locate the implant within the posterior chamber of the eye. The optic 42 contains a curved surface on one side and a plano surface on the other side.

Referring now to FIG. 4, there is shown a plan view of the implant 40 illustrating a pair of arcuate ridges 46 and 48 located along the periphery on the plano surface of implant 40.

Arcuate ridge 46 has a height that varies from a minimum at one end 50 to a maximum at the centermost portion 52 and then varies to a minimum height at end 54. In a similar fashion the arcuate ridge 48 varies from a minimum height at end 56 to a maximum at the centermost portion 58 and then again varies to a minimum height at end 60.

In the preferred embodiment arcuate ridges 46 and 48 each define an arc of approximately 120 degrees and are centrally located on the plano surface of implant 40. In this fashion a space on the periphery of the plano surface of approximately 60 degrees is defined between end point 54 of ridge 46 and end point 56 of ridge 48. In a similar fashion a space defining 60 degrees on the periphery of the plano surface is defined between end point 50 of ridge 46 and end point 60 of ridge 48. This space between the end point 54 and 56 and the space between 50 and 56 provides an even surface for the surgeon to grasp the implant with his forceps, thereby eliminating the tiddly-wink effect that results when the surgeon grasps the implant along the defined ridges which is so common in the prior art devices.

In the preferred embodiment the minimum height of the ridges as at points 54 and 50 on ridge 46 and points 56 and 60 on ridge 48 are approximately 0.1 millimeters high and that height varies to a maximum of 0.3 millimeters at the centermost portion as indicated at point 52 on ridge 46 and at point 58 on ridge 48. The variable height on both ridges 46 and 48 is continuous and approximates that of a camming surface varying from a minimum at each end to a maximum at the centermost portion of each ridge.

Referring now to FIG. 4a, there is shown a cross-sectional view of the end point 56 showing the minimum height of the ridge approximating 0.1 millimeters.

Referring now to FIG. 4b, there is shown the maximum height of the ridge as at point 58 on ridge 48 showing an approximately height of 0.3 millimeters.

FIG. 4c illustrates the minimum height of point 60 of ridge 48 having an approximate height of 0.1 millimeters.

In a similar manner FIG. 4a also illustrates the height at end point 54, whereas FIG. 4b illustrates the height of the centermost portion 52 and FIG. 4c illustrates the height at end point 50 of ridge 46.

Referring now to FIG. 5, there is shown a side view of implant 40 showing a curved surface 66 on one side and the plano surface 68 on the other side. The variable height ridge 58 is also illustrated and shows the maximum height of the ridge at the centermost portion at 58 and the minimum height at end portions 56 and 60, respectively.

Referring now to FIG. 6, there is shown a cross-sectional view of the eye 10 illustrating how the surgeon utilizing a pair of forceps 70 and holding the implant 40 is able to force the haptic 43a through the incision 32 and over that portion of the iris 30a closest to the incision and under that portion of the iris 30b furtherest from the incision.

The forceps 70 are holding the implant 40 in that portion of the implant 40 defined by the 60 degree spacing between end points 54 and 56 of ridges 46 and 48 or in the alternative in that 60 degree portion of the implant 40 defined by the arcuate space between minimum points 50 and 60 of ridges 46 and 48. The important feature is that now the surgeon by using his forceps 70 can hold the implant 40 in a fixed grip and completely eliminate the tiddly-wink effect that generally occurs when an attempt is made to hold the implant on the ridge portion.

It is also interesting to note in FIG. 6 that by holding the implant as indicated the surgeon in pushing the implant 40 over that portion of the iris 30a near the incision 32 contacts the iris at the mininum height portion of the ridges which is either 54 and 56 or at 50 and 60, depending only on where the surgeon grasps the implant 40.

Pushing the implant 40 over the iris 30a allows the variable height ridges 46 and 48 to gently urge the iris down thereby allowing the surgeon to move the implant into the desired portion.

This procedure is repeated again when the implant 40 is finally put in place since the other edge of the ridges 46 and 48 must again slide over that portion of iris 30a as the implant is finally placed in position.

Regardless of where the surgeon grasps the implant 40, the camming action over the iris 30a will be gentle and will result in a minimum of trauma to the delicate iris tissue.

Referring now to FIG. 7, there is shown a cross-sectional view of the eye 10 illustrating how the implant 40 is held centrally located in the posterior chamber by means of haptics 43a and 43b. The plano surface of the implant 40 is maintained in a spaced-apart relationship with respect to the posterior surface 36 of capsule 22 by means of the variable height ridges 46 and 48.

The variable height ridges on the implant provide a mechanism that allows a minimum insertion in the cornea due to the camming action of the variable height ridges as it enters the incision and passes over the iris, thereby minimizing infection and minimizing any traumatizing effect to the delicate iris membranes.

Since the implant is maintained in a spaced-apart relationship with respect to the posterior surface of the capsule, it is now possible to use the Yag laser to destroy any opaqueness caused by migrating pearls without affecting, destroying or influencing the plano surface of the implant.

I claim:

1. A lens implant having a curved side and a plano side comprising:
    at least two arcuate ridges in continuous contact with and located along the periphery of said plano side for supporting the centermost portion of said implant in a spaced-apart relationship, and in which
    each of said ridges has a variable height that varies continuously and gradually from a minimum height at each end to a maximum height at the centermost portion for and each ridge has an arcuate shape measured from the anterior side to the posterior side for reducing trauma to the iris by producing a camming surface without any flat spots on the ridges.

2. A lens according to claim 1 in which said minimum height is approximately 0.1 millimeters high and said maximum height is approximately 0.3 millimeters high.

3. A lens according to claim 1 in which each arcuate ridge describes an arc of substantially 120 degrees.

4. A lens according to claim 1 in which the space between each arcuate ridge describes an arc of substantially 60 degrees.

5. A lens implant comprising:
    a cylindrical optic having a curved side and a plano side,
    said plano side having at least two arcuate ridges in continuous contact with and located along the periphery for supporting the centermost portion of said implant in a spaced-apart relationship,
    each of said ridges having a variable height that varies continuously and gradually from a minimum height at each end to a maximum height at the centermost portion and each ridge has an arcuate shape measured from the anterior side to the posterior side for reducing trauma to the iris by producing a camming surface without any flat spots on the ridges, and
    at least two haptics attached to said optic for supporting and locating said lens.

* * * * *